United States Patent [19]

Pinza et al.

[11] Patent Number: 5,200,406
[45] Date of Patent: Apr. 6, 1993

[54] PHARMACEUTICALLY USEFUL 2,5-DIOXO-1H-OCTAHYDROIMIDAZO[1,2-A]AZEPINES

[75] Inventors: Mario Pinza, Milan; Alberto Cerri, Vigevano Pavia; Carlo Farina, Valsolda Como; Maria T. Riccaboni, Milan, all of Italy

[73] Assignee: I.S.F. Societa per Azioni, Italy

[21] Appl. No.: 862,855

[22] Filed: Apr. 3, 1992

Related U.S. Application Data

[62] Division of Ser. No. 669,806, Mar. 15, 1991, Pat. No. 5,130,319, which is a division of Ser. No. 307,012, Feb. 6, 1989, Pat. No. 5,053,422.

[30] Foreign Application Priority Data

Feb. 8, 1988 [IT] Italy ................... 19336 A/88

[51] Int. Cl.$^5$ ............... A61K 31/415; C07D 487/04
[52] U.S. Cl. .................................. 514/214; 540/521
[58] Field of Search ..................... 540/521; 514/214

[56] References Cited

U.S. PATENT DOCUMENTS

| | | | |
|---|---|---|---|
| 3,334,099 | 8/1967 | Houlihan | 540/521 |
| 4,582,838 | 4/1986 | Butler et al. | 514/322 |
| 4,677,098 | 6/1987 | Butler et al. | 514/63 |

Primary Examiner—Bernard Dentz
Attorney, Agent, or Firm—Dara L. Dinner; Stuart R. Suter; Edward T. Lentz

[57] ABSTRACT

Imidazole derivatives are described which are useful in restoring learning and treating memory difficulties. A compound of the invention is 2,5-dioxohexahydro-1H-pyrrolo[1,2-a]imidazole.

8 Claims, No Drawings

PHARMACEUTICALLY USEFUL 2,5-DIOXO-1H-OCTAHYDROIMIDAZO[1,2-A]AZEPINES

This is a division of application Ser. No. 07/669,806 filed Mar. 15, 1991 now U.S. Pat. No. 5,130,319 which is a division of application Ser. No. 07/307,012 filed Feb. 6, 1989 now U.S. Pat. No. 5,053,422.

The present invention relates to novel compounds, processes for their preparation, pharmaceutical compositions containing them and their use in therapy, in particular as nootropic agents.

Compounds having nootropic activity are known in the art. In particular, 4-substituted derivatives of 2-oxo-1-pyrrolidineacetamide are valued psychotropic agents that restore cognitive function that has been damaged as a result of various pathologies. These drugs are described for example in Pharm. Res. Commun., 16, 67, (1984) by Banfi et al and in Drug Development Res.; 2, 447 (1982) by Itil et al. A particularly well known member of the above-noted class is 4-hydroxy-2-oxo-1-pyrrolidine acetamide (oxiracetam).

It has now been found that certain perhydroazacycloalka[1,2-a]imidazole derivatives also demonstrate psychotropic properties and are expected to be of use as nootropic agents.

The present invention therefore provides, in a first aspect, compounds of structure (1)

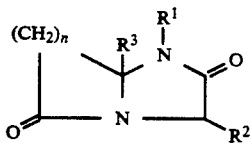

in which, $R^1$ is hydrogen, $C_{1-4}$alkyl, $CHR^6CONHR^7$ or $CHR^6COOR^7$ in which $R^6$ and $R^7$ are each hydrogen or $C_{1-4}$alkyl;

$R^2$ is hydrogen, $C_{1-5}$alkyl or any residue $R^2$ of an amino acid $R^2CH(NH_2)COOH$ $R^3$ is hydrogen, $C_{1-4}$alkyl, $CONH_2$ or $CO_2R^8$ in which $R^8$ is hydrogen or $C_{1-4}$alkyl; and n is 2, 3 or 4.

Suitably $R^1$ and $R^3$ are each $C_{1-4}$alkyl and $R^2$ is $C_{1-5}$alkyl. More suitably two of $R^1$ to $R^3$ are hydrogen and the third is other than hydrogen. Preferably $R^1$ to $R^3$ are each hydrogen. Preferably n is 2. Suitable groups $R^2$ which are any residue $R^2$ of a amino acid $R^2CH(NH_2)CO_2H$, include for example $CH_3$, $(CH_3)_2CH$, $PhCH_2$, $CH_2OH$, $CH_2CH_2CONH_2$ and $CH_2COOH$.

$C_{1-4}$ and $C_{1-5}$alkyl groups can be straight or branched, in particular methyl, ethyl or isobutyl.

Particular compounds of the present invention include, for example,
2,5-dioxohexahydro-1H-pyrrolo[1,2-a]imidazole;
2,5-dioxo-7a-methylhexahydro-1H-pyrrolo[1,2-a]imidazole;
2,5-dioxo-3-methylhexahydro-1H-pyrrolo[1,2-a]imidazole;
2,5-dioxo-3-isobutylhexahydro-1H-pyrrolo[1,2-a]imidazole;
2,5-dioxo-1-ethylhexahydro-1H-pyrrolo[1,2-a]imidazole;
2,5-dioxo-3,7a-dimethylhexahydro-1H-pyrrolo[1,2-a]imidazole;
ethyl 2,5-dioxohexadro-1H-pyrrolo[1,2-a]imidazole-1-acetate;
2,5-dioxohexadro-1H-pyrrolo[1,2-a]imidazole-1-acetamide;
(3-L)-3-benzyl-2,5-dioxhexahydro-1H-pyrrolo[1,2-a]imidazole;
(3-L)-3-hydroxymethyl-2,5-dioxohexahydro-1H-pyrrolo [1,2-a]imidazole;
2,5-dioxohexahydro-1H-pyrrolo[1,2-a]imidazole-7a-carboxylic acid;
ethyl 2,5-dioxohexahydro-1H-pyrrolo[1,2-a]imidazole-7a-carboxylate;
2,5-dioxohexahydro-1H-pyrrolo[1,2-a]imidazole-7a-carboxamide;
2,5-dioxooctahydro-1H-imidazo[1,2-a]pyridine;
2,5-dioxooctahydro-1H-imidazo[1,2-a]azepine.

It will be appreciated that certain of the compounds of structure (I) can contain one or more chiral centres. The present invention covers all optical isomers of these compounds in their fully and partially resolved forms and in the form of racemic mixtures.

The present invention therefore provides in a further aspect, a process for the preparation of compounds of structure (1) which comprises:

a) reaction of a compound of structure (2) with a compound of structure (3):

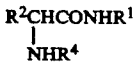

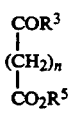

in which $R^1$ to $R^3$ and n are as described for structure (1), $R^4$ is hydrogen and $R^5$ is hydrogen, $C_{1-4}$alkyl or benzyl; or b) cyclization of a compound of structure (4)

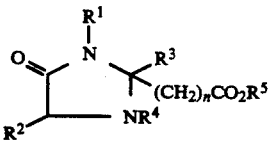

in which $R^1$ to $R^3$ and n are as described for structure (1), $R^4$ is hydrogen and $R^5$ is hydrogen, $C_{1-4}$alkyl or benzyl.

Suitably the reaction between compounds of structure (2) and (3) is carried out by heating in a suitable solvent and in the presence of a base, such as an alkali metal alkoxide, when compound (2) is employed in the form of an acid addition salt (e.g. hydrochloride). Preferably the reaction is carried out at reflux in water as a solvent.

Suitably, the cyclization of a compound of structure (4) when $R^4$ is hydrogen and $R^5$ is alkyl or benzyl is carried out by heating the compound, optionally under reduced pressure, in the presence or absence of solvent. Preferably, the cyclization is effected by heating the compound of structure (4) in water at reflux temperature. When $R^5$ is hydrogen, cyclization will require activation of the carboxyl group or the use of a peptide coupling reagent in a dipolar aprotic solvent.

Suitable methods for activating carboxyl groups and suitable peptide coupling reagents are all well known to the art and are described for example in "Peptide Synthesis" by M. Bodansky, Y. Klausner and M. Ondetti (Wiley 1976) and in "Protective Groups in Organic Synthesis" by T. W. Greene (Wiley, 1981). Examples of activated derivatives of carboxyl groups are acyl chlorides, acyl azides, mixed anhydrides (e.g. formed with an alkyl chloroformate or pivaloyl chloride) and activated esters (e.g. trichlorophenyl, N-hydroxysuccinimido and 1-hydroxybenzotriazole esters). Examples of peptide coupling reagents are carbodiimides and Woodward's Reagent K (N-ethyl-5-phenylisoxazolium-3'-sulphonate).

Suitable dipolar aprotic solvents are tetrahydrofuran, acetonitrile, dimethylformamide or dimethylsulfoxide.

Preferably the cyclization of a compound of structure (4) in which $R^4$ is hydrogen and $R^5$ is $C_{1-4}$ alkyl or benzyl is carried out in a suitable solvent, such as methanol, in the presence of ammonium hydroxide at moderate temperatures of about 50° C. and for short reaction times of about 1 hour, or until reaction is complete. Such cyclization produces the compounds of structure (I) in high yields, is novel, and forms a further aspect of the invention.

The starting compounds (2), (3) and (4) can be prepared by methods known to those skilled in the art or analogous to those known in the art; for example, compounds of structure (2) in which $R^1$ and $R^4$ are hydrogen and $R^2$ is methyl or isobutyl can be prepared by procedures described in J. Am. Chem. Soc., 53, 3183 [1931] and 79, 4686, [1957]; compounds of structure (2) in which $R^1$ and $R^4$ are hydrogen and $R^2$ is $CH_2OH$ can be prepared by procedures described in J. Biol. Chem., 212, 271 [1955]; compounds of structure (2) in which $R^1$ is ethyl and $R^2$ and $R^4$ are hydrogen can be prepared by the method described in Chem. Ber., 89, 1363, [1956]; for example of structure (3) in which $R^3$ is methyl, $R^5$ is ethyl and n is 2 can be prepared by the procedure described in J. Prakt. Chem. 1 (4), 153 [1955]; compounds of structure (3) in which $R^3$ is hydrogen, $R^5$ is ethyl and n is 2 can be prepared by the procedure described in J. Pharm. Soc. Japan, 75, 622 [1955]; compounds of structure (3) in which $R^3$ is hydrogen, $R^5$ is methyl and n is 3 can be prepared by the procedure described in Synthesis, 1982, 881; compounds of structure (3) in which $R^3$ is hydrogen, $R^5$ is methyl and n is 4 can be prepared by the procedure described in J. Org. Chem., 53, 1064 [1988].

Compounds of structure (3) in which $R^3$ is hydrogen $R^5$ is isobutyl and n is 2 can be prepared by reduction of a compound of structure $HCOCH=CHCO_2iBu$. This process is new and forms a further aspect of the present invention. Suitably the reaction is carried out in a $C_{1-4}$alkanol, in the presence of a noble metal catalyst at atmospheric pressure; preferably the reaction is carried out in 96% ethanol in the presence of a 5% palladium on charcoal catalyst.

Compounds of the structure (4) in which $R^4$ is hydrogen can be prepared by hydrogenation of compounds of structure (5)

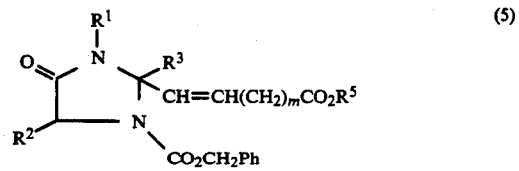

in which $R^1$ to $R^3$ are as described for structure (1) m is 0, 1 or 2 and $R^5$ is hydrogen or $C_{1-4}$alkyl or benzyl; or directly from the appropriate compounds of structure (2) in which $R^4$ is hydrogen and (3). Alternatively, compounds of structure (4) in which $R^4$ is hydrogen can be obtained by catalytic hydrogenation of compounds of structure (4) in which $R^4$ is benzyl, which, in turn, can be prepared from the appropriate compounds of structure (2), in which $R^4$ is benzyl, and (3). Suitably the hydrogenations are carried out under conditions which remove the N-protecting groups and also reduce the side-chain double bond, when present, for example by using a noble metal catalyst, such as palladium on charcoal in a suitable solvent, such as ethanol. When $R^5$ is benzyl, compound (4) in which $R^5$ is hydrogen is directly obtained.

Compounds of structure (5) can themselves be prepared by reaction between compound of structure (2) in which $R^4$ is $PhCH_2OCO$ and an appropriate carbonyl compound of structure (6)

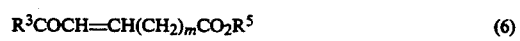

in which $R^3$, $R^5$ and m are as hereinbefore described.

The reaction is carried out in a suitable solvent at elevated temperature, optionally in the presence of a suitable catalyst. Preferably the reaction is carried out in toluene at elevated temperature, in the presence of p-toluenesulphonic acid monohydrate as described in, Tetrahedron, 41, 611, 1985.

The starting compounds (2) in which $R^4$ is $PhCH_2$ or $PhCH_2OCO$ and (6) can be prepared by methods known to those skilled in the art or analogous to those known in the art; for example compounds of structure (2) in which $R^1$ and $R^2$ are hydrogen and $R^4$ is $PhCH_2OCO$ can be prepared by procedures described in J. Am. Chem. Soc., 73, 2936 [1951], compounds of structure (2) in which $R^1$ and $R^2$ are hydrogen and $R^4$ is benzyl can be prepared by procedures described in Synthesis, 1983, 329; and, for example, compounds of structure (6) in which $R^3$ is hydrogen, $R^5$ is ethyl and m is 2 can be prepared by procedures described in J. Pharm. Soc. Japan, 75, 622 [1955]; compounds of structure (6) in which $R^3$ is methyl, $R^5$ is methyl and m is 0 can be prepared by the procedure described in J. Am. Chem. Soc., 68, 2510 [1946]; compounds of structure (6) in which $R^3$ is methyl, $R^5$ is ethyl and m is 0 can be prepared by procedures described in Annalen der Chemie, 264, 248 [1891]. In particular compound (6) in which $R^3$ is hydrogen, $R^5$ is isobutyl and m is 0 can be prepared by base catalyzed rearrangement of isobutyl 3,4-epoxybutanoate (whose preparation is described in E.P. Appl. 154,490) and subsequent oxidation with methods known to those skilled in the art or analogous to those known in the art; for example with a transition metal compound as described in "Oxidation" Vol. 1, by D. G. Lee; R. L. Augustine Ed., (Dekker 1969).

The compounds of structure (1) are of use as therapeutic agents and in particular have nootropic activity, that is to say they help restore learning and memory difficulties associated with ageing and various pathologies including for example Alzheimer's disease.

The present invention therefore provides, in a further aspect a method of restoring learning and treating memory difficulties which comprises administering to a mammal in need thereof a non-toxic effective amount of a compound of structure (1). The cognitive disorders occurring in such pathologies are known to be related to deficits in the brain cholinergic system as shown both by morphological (B. E. Tomlinson in "Biochemistry of Dementias"; P. J. Roberts Ed.; John Wiley & Sons, New York, N.Y. p. 15–22, 1980) and neurochemical findings (R. T. Bartus et al., Science, 217, 408, 1982). It is also well known that significant impairments of cognitive functions are the more evident and debilitating symptoms observed in patients with Alzheimer's disease, senile dementia of the Alzheimer type and multiinfarctual dementia. On the other hand, the anticholinergic drug scopolamine, produces in humans (D. A. Drachman, Archs. Neurol., Chicago, 30, 113, 1974) as well as in animals (D. A. Eckerman, Pharmacol. Biochem. Behav., 12, 595, 1980) a significant memory loss, which is directly related to a decrease of acetylcholine concentration in specific cerebral areas such as the cerebral cortex and the hippocampus. On the basis of these premises, compounds of structure 1 have been specifically tested in rats against both the disruptive action of scopolamine on mnestic trace and on the reduction of acetylcholine levels in hippocampus. To evaluate the effect on memory and learning, one trial-step through-passive avoidance test in male Wistar rats (150–160 g) was used. The equipment was essentially the same described by Essman (Pharmacol. Res. Commun., 5, 295, 1973).

The passage from a light box into a dark one was punished by unavoidable electric foot shocks. The animals must learn to avoid, after a single learning session, the crossing from the light to the dark box. Thirty minutes after the first session (learning session), the learning effect was quantified (retest session) by means of the latencies (in seconds) between the admission of animals into the light box and the entering into the dark one. The learning effect is substantially impaired by a treatment with scopolamine (0.63 mg/kg s.c.) sixty minutes before the learning session. Saline or the test compounds were administered i.p. thirty minutes before scopolamine. The control group was treated in the same way but with saline only. For example, results on compounds A (1, $R^1=R^2=R^3=H$ and n=2), B (1, $R^1=R^2=H$, $R^3=Me$ and n=2) and (1, $R^1$, =H, $R^2=R^3=Me$, n=2 and the configuration at carbon in 3 position is S) in comparison with oxiracetam are given in Table 1.

TABLE 1

One-trial step through passive avoidance test in rats: activity of compound A and oxiracetam against amnesia induced by scopolamine (0.63 mg/kg s.c.)

| Treatment[a] | Dose mg/kg i.p. | Latencies Learning session | Retest session | Difference[b] |
|---|---|---|---|---|
| SALINE | — | 21.3 | 118.3 | 97.0** |
| SCOPOLAMINE | — | 20.3 | 72.5 | 52.2 |
| A + SCOPOLAMINE | 0.1 | 20.9 | 100.5 | 79.6* |
| A + SCOPOLAMINE | 0.3 | 19.7 | 103.6 | 83.9* |
| A + SCOPOLAMINE | 1 | 19.7 | 120.0 | 100.3** |
| B + SCOPOLAMINE | 0.1 | 20.4 | 98.4 | 78.0* |
| B + SCOPOLAMINE | 0.3 | 18.6 | 102.3 | 83.7* |

TABLE 1-continued

One-trial step through passive avoidance test in rats: activity of compound A and oxiracetam against amnesia induced by scopolamine (0.63 mg/kg s.c.)

| Treatment[a] | Dose mg/kg i.p. | Latencies Learning session | Retest session | Difference[b] |
|---|---|---|---|---|
| B + SCOPOLAMINE | 1 | 21.1 | 119.0 | 97.9** |
| C + SCOPOLAMINE | 0.1 | 20.3 | 96.4 | 76.1* |
| C + SCOPOLAMINE | 0.3 | 21.3 | 107.5 | 86.2* |
| C + SCOPOLAMINE | 1 | 19.5 | 120.0 | 100.5** |
| OXIRACETAM + SCOP. | 3 | 21.5 | 78.0 | 56.5 n.s. |
| OXIRACETAM + SCOP. | 10 | 19.7 | 115.0 | 95.3** |
| OXIRACETAM + SCOP. | 30 | 19.1 | 120.0 | 100.9** |

[a]Twenty rats were used for each experimental group
[b]cut-off time = 120 sec.
*Dunnett's test less than 0.05 versus scopolamine
**Dunnett's test less than 0.01 versus scopolamine When used in the therapeutic treatment of humans and animals, the compounds of structure (1) are normally formulated in accordance with standard pharmaceutical practice as a pharmaceutical composition. Therefore in another aspect the present invention there is provided a pharmaceutical composition which comprises a compound of structure (1) or a pharmaceutically acceptable salt thereof and a pharmaceutically acceptable carrier.

The compounds of the structure (1) may be administered in standard manner for the treatment of the indicated diseases, for example orally, parenterally, rectally, transdermally or by transmucosal (for example sub-lingual, or buccal or insufflatory) administration.

The compounds of the structure (1) which are active when given orally or via sub-lingual or buccal administration can be formulated as syrups, tablets, capsules and lozenges. A syrup formulation will generally consist of a suspension or solution of the compound or salt in a liquid carrier for example, ethanol, glycerine or water with a flavouring or colouring agent. Where the composition is in the form of a tablet, any pharmaceutical carrier routinely used for preparing solid formulations may be used. Examples of such carriers include magnesium stearate, starch, lactose and sucrose. Where the composition is in the form of a capsule, any routine encapsulation is suitable, for example using the aforementioned carriers in a hard gelatin capsule shell. Where the composition is in the form of a soft gelatin shell capsule any pharmaceutical carrier routinely used for preparing dispersions or suspensions may be utilised, for example aqueous gums, celluloses, silicates or oils and are incorporated in a soft gelatin capsule shell.

Typical parenteral compositions consist of a solution or suspension of the compound of the structure (1) in a sterile aqueous or non-aqueous carrier optionally containing a parenterally acceptable oil, for example polyethylene glycol, polyvinylpyrrolidone, lecithin, arachis oil, or sesame oil.

A typical suppository formulation comprises a compound of structure (1) which is active when administered in this way, with a binding and/or lubricating agent, for example polymeric glycols, gelatins, cocoabutter or other low melting vegetable waxes or fats.

Typical transdermal formulations comprise a conventional aqueous or non-aqueous vehicle, for example a cream, ointment, lotion or paste or can be in the form of a medicated plaster, patch or membrane.

Preferably the composition is in unit dosage form, for example a tablet or capsule, so that the patient may administer to himself a single dose.

Oxiracetam is a compound which is used in the treatment of senile dementia and related disease conditions. The compounds of structure (1) can be administered in similar regimes to those established for oxiracetam with any appropriate adjustment in dose levels or frequency of dosing having regard to the greater activity and better pharmacological profile of the compounds of structure (1).

Each dosage unit for oral administration contains suitably from 0.05 mg/Kg to 20 mg/Kg, and preferably from 0.1 mg/Kg to 5 mg/Kg, and each dosage unit for parenteral administration contains suitably from 0.05 mg/Kg to 10 mg/Kg, of a compound of structure (1).

The daily dosage regimen for oral administration is suitably about 0.05 mg/Kg to 50 mg/Kg, more suitably about 0.1 mg/Kg to 20 mg/Kg of a compound of structure (1). The active ingredient may be administered from 1 to 6 times daily. The compounds of structure (1) may be co-administered with other pharmaceutically active compounds, for example in combination, concurrently or sequentially, particularly with other compounds used in the treatment of elderly patients e.g. tranquillisers, diuretics, antihypertensives, vasodilators and inotropic agents.

The invention is illustrated by the following Examples.

Preparation 1

A) Isobutyl (E)-4-hydroxy-2-butenoate

To an ice cold solution of isobutyl 3,4-epoxybutanoate (300 g, 1.9 mol) in toluene (2.5 l), sodium hydride (55% suspension in oil, 3 g, 0.07 mol) was added portionwise. The solution was stirred at 0°–5° C. for 1 hour, then 55% sodium hydride (3 g, 0.07 mol) was added again. After stirring at room temperature for 1 hour the solution was washed with brine (0.4 l) containing 10% hydrochloric acid (60 ml), then twice with brine (300 ml each). The organic solution was dried over anhydrous sodium sulfate and evaporated to dryness. Distillation of the residue afforded 175 g (58.3%) of the title compound as a colourless oil, b.p. 89°–90° C. (0.5 mmHg). NMR (CDCl$_3$): delta$_H$=7.05 (dt, J=15 and 4 Hz, 1H, CH=CH—CO), 6.12 (dt, J=15 and 2 Hz, 1H, CH=CH—CO), 4.40 (c.a, 2H, CH$_2$OH). MS (E.I., 70 eV, 1.5 mA) m/z=127 (M-CH$_2$OH)$^+$, 85 (M-C$_3$H$_5$O$_2$)$^+$.

B) Isobutyl (E)-4-oxo-2-butenoate

To a suspension of pyridinium chlorochromate (100 g, 0.463 mol) in dichloromethane (350 ml), a solution of isobutyl (E)-4-hydroxycrotonate (50 g, 0.316 mol) in dichloromethane (150 ml) was added. The internal temperature gradually rose to 40° C. and stirring was continued for 2 hours without cooling. Diethyl ether (0.9 l) was added and the supernatant was decanted from the black gum. The insoluble residue was washed twice with 300 ml portions of diethyl ether. The combined organic solutions were passed through a short pad of Florisil and the solvent was removed by distillation, to yield 45.3 g (91.6%) of the title compound, as a pale yellow oil, Rf=0.5 (silica gel plates, cyclohexane-ethyl acetate 6:4). NMR (CDCl$_3$): delta$_H$=9.80 (ABX, 1H, CHO), 6.98 and 6.75 (ABX, J$_{AB}$=15 Hz, 2H, CH=CH). MS (E.I., 70 eV, 1.5 mA) m/z=155 (M-H)$^+$, 85 (M-C$_3$H$_3$O$_2$)$^+$.

C) Isobutyl 4-oxobutanoate

To a solution of isobutyl (E)-4-oxo-2-butenoate (97 g, 0.62 mol) in 96% ethanol (800 ml), 5% palladium on charcoal (9.7 g) was added and hydrogen was bubbled at 5°–10° C. and at atmospheric pressure for 20 hours. Removal of the catalyst and evaporation of the solvent gave 97.6 g (99%) of the title compound; Rf=0.41 (silica gel plates, eluent: cyclohexane-ethyl acetate 6:4). NMR (CDCl$_3$): delta$_H$=12.5 (d, J=1 Hz, 1H, CHO); 3.85 (d, J=6 Hz, 2H, COOCH$_2$); 2.80-2.40 (c.a., 4H, CH$_2$CH$_2$CO); 2.10-1.70 (c.a., 1H, CH$_2$CHMe$_2$); 0.90 (d, J=6 Hz, 6H, CH$_3$). MS (E.I., 70 eV, 1.5 mA) m/z=103 (M-C$_3$H$_3$O)$^+$, 85 (M-C$_3$H$_5$O$_2$)$^+$, 57 (M-C$_4$H$_5$O$_3$)$^+$.

EXAMPLE 1

A) Isobutyl (E)-1-benzyloxycarbonyl-4-oxo-2-imidazolidineacrylate

To a solution of isobutyl (E)-4-oxo-2-butenoate (11 g, 70.43 mmol) in toluene (170 ml) benzyloxycarbonylglycinamide (14.67 g, 70.43 mmol) and p-toluensulfonic acid monohydrate (0.67 g, 3.5 mmol) were added. The mixture was refluxed for 4 hours in a Dean-Stark apparatus. The obtained solution was cooled, the precipitate matter was filtered off and the filtrate was washed with a saturated solution of sodium hydrogen carbonate (50 ml) and brine (50 ml). The organic phase, dried over anhydrous sodium sulfate, was evaporated to dryness. The residue was chromatographed over silica gel (ethyl acetate-cyclohexane 1:1). The collected fractions were evaporated and the residue, triturated with diisopropyl ether, afforded 7.72 g (31.6%) of the title compound as a white solid, m.p. 97°–100° C. NMR (CDCl$_3$): delta$_H$=6.80 (ABX, J$_{AB}$=15 Hz, J$_{AX}$=7 Hz, 1H, CH=CH—CO), 6.15 (c.a., 1H, CH=CH—CO), 5.70 (ABX, J$_{AB}$=7 Hz, CH=CH—CH), 4.10 and 3.97 (ABq, J=16 Hz, 2H, COCH$_2$N). MS (E.I., 70 eV, 1.5 mA) m/z=346 (M+), 239 (M-C$_7$H$_7$O)$^+$, 91 (C$_7$H$_7$+).

B) Isobutyl 4-oxo-2-imidazolidinepropanoate

To a solution of isobutyl (E)-1-benzyloxycarbonyl-4-oxo-2-imidazolidineacrylate (7.7 g, 22.2 mmol) in 96% ethanol (200 ml), 5% palladium on charcoal (0.5 g) was added and hydrogen was bubbled at 20° C. and at atmospheric pressure for 2 hours. Removal of the catalyst and evaporation of the solvent gave a residue which was triturated with diisopropyl ether to give 4.1 g (86%) of the title compound, m.p. 50°–52° C. NMR (CDCl$_3$): delta$_H$=4.45 (t, J=6 Hz, 1H, N—CH—N), 3.10 (s, 2H, N—CH$_2$—CO). MS (E.I., 70 eV, 1.5 mA) m/z=214 (M+), 157 (M-C$_4$H$_9$)$^+$, 85 (M-C$_7$H$_{13}$O$_2$)$^+$.

C) 2,5-Dioxohexahydro-1H-pyrrolo[1,2-a]imidazole

Isobutyl 4-oxo-2 imidazolidinepropanoate (4 g, 18.7 mmol) was stirred at 120°–130° C. (external temperature) under vacuum for 3–5 hours. The residue was triturated with ethyl acetate to yield 0.75 g (28.6%) of the title compound, m.p. 155°–157° C. NMR (CDCl$_3$): delta$_H$=5.45 (t, J=6 Hz, 1H, CH), 4.23 and 3.60 (ABq, J=16 Hz 2H, COCH$_2$N). MS (E.I., 70 eV, 1.5 mA) m/z=140 (M+), 97 (M-CONH)$^+$.

EXAMPLE 2

2,5-Dioxo-7a-methylhexahydro-1H-pyrrolo[1,2-a]imidazole

To a solution of glycinamide hydrochloride (18.4 g, 0.166 mol) in water (200 ml), adjusted to pH 9.5 with 10% sodium hydroxide (about 60 ml), ethyl 4-oxopentanoate (20 g, 0.139 mol) was added. The solution was refluxed for 24 hours. After cooling the solvent was evaporated under vacuum and the residue was chromatographed over silica gel (dichloromethane-methanol 9:1) to afford 4.5 g (21%) of the title compound, m.p. 187°–189° C. NMR (CDCl$_3$): delta$_H$=4.17 and 3.53 (ABq, J=16 Hz, 2H, NCH$_2$CO), 1.5 (s, 3H, CH$_3$). MS (E.I., 70 eV, 1.5 mA) m/z=154 (M+), 139 (M-CH$_3$)+, 111 (M-CONH)+.

EXAMPLE 3

(3S)-3,7a-Dimethyl-2,5-dioxohexahydro-1H-pyrrolo[1,2-a]imidazole

L-Alaninamide hydrochloride (20.7 g, 0.166 mol) and ethyl 4-oxopentanoate (20 g, 0.13 mol) were reacted together according to the procedure of Example 2 to give the title compound, 4.5 g (19.1%), m.p. 228°–230° (with decomposition), [alpha]$_D$=+50.7° (c=3, H$_2$O). NMR (CDCl$_3$): delta$_H$=7.95 (bs, 1H, NH); 4.30 (q, J=8 Hz, 1H, CHCH$_3$); 3.00–2.10 (c.a., 4H, CH$_2$CH$_2$); 1.60 (s, 3H, C-CH$_3$; 1.45 (d, J=8 Hz, 3H, CH$_3$CH). MS (E.I., 70 eV, 1.5 mA) m/z=168 (M+), 153 (M-CH$_3$)+, 125 (M-CHNO)+, 112 (M-C$_3$H$_4$O)+.

EXAMPLE 4

(3R,S)-3,7a-Dimethyl-2,5-dioxohexahydro-1H-pyrrolo[1,2-a]imidazole

DL-Alaninamide hydrochloride (6.9 g), 0.055 mol) and ethyl 4-oxopentanoate (6.7 g, 0.043 mol) were reacted together according to the procedure of Example 2 to give the title compound, 1.65 g (22.8%), m.p. 184°–192°. NMR (DMSO-d$_6$: delta$_H$=8.80 (bs, 1H, NH); 3.90 (q, J=7.5 Hz, 1H, CHCH$_3$) 3.00–2.00 (c.a., 4H, CH$_2$CH$_2$); 1.42 (s, 3H, C—CH$_3$); 1.22 (d, J=7.5 Hz, 1H, CHCH$_3$)

EXAMPLE 5

A) Isobutyl (4S)-4-methyl-5-oxo-2-imidazolidinepropanoate

To a suspension of L-alaninamide hydrochloride (2.4 g, 19.3 mmol) in butanol (20 ml) isobutyl 4-oxobutanoate (3 g, 18.96 mmol) and sodium carbonate (1 g, 9.4 mmol) were added and the mixture was refluxed for 7 hours. After cooling the precipitate was filtered off and the filtrate was evaporated to dryness. The residue was chromatographed over silica gel (dichloromethane-methanol 9:1) to afford 0.87 g (20%) of the title compound. Hydrochloride salt: m.p. 146°–148° C. (with decomposition). NMR (DMSO-d$_6$): delta$_H$=9.20 (bs, 1H, CONH); 4.80 (t, J=6 Hz, 1H, HN—CH—NH); 4.00 (q, J=8 Hz, 1H, CHCH$_3$); 3.83 (d, J=6 Hz, 2H, COOCH$_2$); 3.40 (bs, 1H, CHNHCH); 2.90–2.65 (c.a., 2H, CH$_2$CO); 2.25–1.75 (c.a., 3H, CH$_2$CH$_2$CO and CH(CH$_3$)$_2$); 1.37 (d, J=6 Hz, 3H, CH$_3$CHNH); 0.87 (d, J=6 Hz, 6H, CH(CH$_3$)$_2$). MS (E.I., 70 eV, 1.5 mA) m/z=228 (M+), 171 (M-C$_4$H$_9$)+, 155 (M-C$_4$H$_9$O)+, 99 (M-C$_7$H$_{13}$O$_2$)+.

B) (3S)-2,5-Dioxo-3-methylhexahydro-1H-pyrrolo[1,2a]imidazole

Isobutyl (4S)-4-methyl-5-oxo-2-imidazolidinepropanoate (0.870 g, 3.8 mmol) was stirred without solvent at 110°–120° C. (external temperature) for 5 hours. The residue was chromatographed over silica gel (dichloromethane methanol 9:1). The collected fractions were evaporated and the residue was triturated with diethyl ether, to afford 0.4 q (68.2%) of the title compound, m.p. 126°–129° C. NMR (CDCl$_3$): delta$_H$=8.02 (bs, 1H, CONH); 5.35 (t, J=5 Hz, 1H, NCHNH); 4.30 (q, J=8 Hz, 1H, NCHCH$_3$); 2.90–1.80 (c.a., 4H, COCH$_2$CH$_2$); 1.38 (d, J=8 Hz, 3H, CH$_3$CH). MS (E.I., 70 eV, 1.5 mA) m/z=154 (M+), 139 (M-CH$_3$)+, 111 (M-CHNO)+, 98 (M-C$_3$H$_4$O)+.

EXAMPLE 6

(3R,S)-2,5-Dioxo-3-methylhexahydro-1H-pyrrolo[1,2-a]imidazole

DL-Alaninamide hydrochloride (6.9 g, 0.055 mol) and isobutyl 4-oxobutanoate (7.3 g, 0.046 mol) were reacted together according the procedure of Example 2 to give the title compound, 1.7 g (24%), m.p. 84°–86°. NMR (DMSO-d$_6$): delta$_H$=8.55 (bs, 1H, NH); 5.20 (t, J=5 Hz, NCHNH); 3.92 (q, J=6.5 Hz, 1H, CHCH$_3$); 2.82–1.50 (c.a., 4H, CH$_2$CH$_2$); 1.17 (d, J=6.5 Hz, 3H, CHCH$_3$). MS (E.I., 70 eV, 1.5 mA) m/z=154 (M+), 111 (M-CHNO)+, 98 (M-C$_3$H$_4$O)+.

EXAMPLE 7

A) Isobutyl (4S)-4-isobutyl-5-oxo-2-imidazolidinepropanoate

L-Leucinamide hydrochloride (3.2 g, 19.2 mmol) and isobutyl 4-oxobutanoate (3 g, 18.96 mmol) were reacted together according to the procedure of example 5A to give the title compound, 1.7 g (33%).

Hydrochloride salt: m.p. 187°–188° C. (with decomposition). NMR (DMSO-d$_6$) delta$_H$=9.23 and 9.18 (bs, 1H, CONH); 4.92 and 4.85 (t, J=6 Hz, 1H, NHCHNH); 4.10–3.80 (c.a., 1H, COCHNH); 3.82 (d, J=6 Hz, 2H, COOCH$_2$); 2.70–2.40 (c.a., 2H, CH$_2$CO); 2.20–1.55 (c.a., 6H, CHCH$_2$CH(CH$_3$)$_2$, NHCHCH$_2$CH$_2$ and COOCH$_2$CH(CH$_3$)$_2$); 0.92 and 0.87 (d, J=6 Hz, 12H, CH(CH$_3$)$_2$). MS (E.I., 70 eV, 1.5 mA) m/z=270 (M+), 213 (M-C$_4$H$_9$)+, 141 (M-C$_7$H$_{13}$O$_2$)+.

B) (3S)-2,5-Dioxo-3-isobutylhexahydro-1H-pyrrolo[1,2-a]imidazole

Isobutyl (4S)-4-isobutyl-5-oxo-2-imidazolidine propanoate (1.4 g, 5.4 mmol) was heated at 130°–140° C. (external temperature) for 5 hours. Chromatography of the residue over silica gel (dichloromethane-methanol 9:1) gave the title compound, 0.45 g (45%) m.p. 156°–157° C. NMR (CDCl$_3$): delta$_H$=7.35 (bs, 1H, CONH); 5.30 (t, J=6 Hz, 1H, NCHNH); 4.22 (c.a., 1H, NCHCO); 2.75–1.40 (c.a., 7H, CH$_2$CH$_2$ and CHCH$_2$CH); 1.03 and 0.90 (d, J=6 Hz, 6H, CH$_3$). MS (E.I., 70 eV, 1.5 mA) m/z=196 (M+), 140 (M-C$_3$H$_4$O)+, 84 (M-C$_6$H$_{10}$NO)+.

EXAMPLE 8

2,5-Dioxo-1-ethylhexahydro-1H-pyrrolo[1,2-a]imidazole

Glycine ethylamide hydrochloride (2.1 g, 15.1 mmol) and isobutyl 4-oxobutanoate (2 g, 12.6 mmol) were reacted together according the procedure of Example 2 to give the title compound, 0.5 g (23.5%) as a viscous oil. Rf=0.51 (silica gel plates, eluent dichloromethane-methanol 9:1). NMR (CDCl$_3$): delta$_H$=5.27 (t, J=6 Hz, 1H, N—CH—N); 4.20 and 3.45 (ABq, J=17 Hz, 2H, N—CH$_2$—CO); 3.25 (q, J=7 Hz, 2H, NCH$_2$CH$_3$); 2.70-1.75 (c.a., 4H, COCH$_2$CH$_2$CH); 1.12 (t, J=7 Hz, 3H, CH$_3$). MS (E.I., 70 eV, 1.5 mA) m/z=168 (M+), 112 (M-C$_3$H$_4$O)+, 97 (M-C$_4$H$_7$O)+.

EXAMPLE 9

2,5-Dioxohexahydro-1H-pyrrolo[1,2-a]imidazole

Glycinamide hydrochloride (4.2 g, 38 mmol) and isobutyl 4-oxobutanoate (5 g, 31.6 mmol) were reacted together according to the procedure of example 2, to give the title compound 1 g (22.6%), m.p. 154°-157° C.

EXAMPLE 10

Ethyl 2,5-dioxohexadro-1H-pyrrolo[1,2-a]imidazole-1-acetate

A mixture of 2,5-dioxohexahydropyrrolo-1H-[1,2-a]imidazole (0.5 g, 3.57 mmol), tetrabutylammonium bromide (0.57 g, 1,78 mmol) and potassium carbonate (2.5 g, 17.8 mmol) in dry acetonitrile (6 ml) was stirred at room temperature for 1 hour. Ethyl bromoacetate (0.5 ml, 4.53 mmol) was added and the suspension was heated at 60° C. for 2.5 hours. The precipitate was filtered off, the filtrate was evaporated under vacuum and the residue was chromatographed over silica gel (ethyl acetate-acetonemethanol 6:3:1) to afford 0.7 g (92%) of the title compound, m.p. 75°-80° C. NMR (CDCl$_3$): delta$_H$=5.40 (c.a., 1H, N—CH—N); 4.21 (q, J=7.2 Hz, 2H, COOCH$_2$CH$_3$); 4.32 e 3.68 (ABq, J=15.9 Hz, 2H, NCH$_2$CO); 4.30 and 3.80 (ABq, J=17.8 Hz, 2H, —CH$_2$COOEt); 2.80-1.70 (c.a., 4H, CH$_2$CH$_2$) 1.28 (t, J=7.2 Hz, 3H, COOCH$_2$CH$_3$). MS (E.I., 70 eV, 1.5 mA) m/z=226 (M+), 153 (M-CO$_2$Et)+; 140 (M-CH$_2$CO$_2$Et)+.

EXAMPLE 11

2,5-Dioxohexahydro-1H-pyrrolo[1,2-a]imidazole-1-acetamide

A solution of ethyl 2,5-dioxohexahydropyrrolo[1,2-a]imidazole-1-acetate (1.4 g, 6.18 mmol), in methanol (25 ml) was saturated with ammonia at 0° C. After stirring at room temperature for 16 hours the precipitate was collected, washed with methanol and dried to yield 0.9 g (75%) of the title compound, m.p. 182°-185° C. NMR (DMSO-d$_6$): delta$_H$=7.50 and 7.10 (2s, 2H, CONH$_2$); 5.25 (c.a. 1H, N—CH—N); 3.94 and 3.55 (ABq, J=16 Hz, 2H, N—CH$_2$CO); 3.85 and 3.70 (ABq, J=16.5 Hz, 2H, N—CH$_2$CONH$_2$); 2.90 and 1.90 (c.a., 4H, CH$_2$CH$_2$). MS (E.I., 70 eV, 1.5 mA) m/z=139 (M-CH$_2$CONH$_2$)+.

EXAMPLE 12

A) Isobutyl (4S)-4-benzyl-5-oxo-2-imidazolidinepropanoate

To a solution of L-phenylalaninamide hydrochloride (20 g, 0.1 mol) in water (200 ml), adjusted to pH 8.2 with 10% sodium hydroxide (about 35 ml), was added isobutyl 4-oxobutanoate (16 g, 0.1 mol). The solution was refluxed for 24 hours. After cooling, the solution was extracted with dichloromethane (4×200 ml). The organic phase was dried and evaporated to dryness under vacuum. The residue was chromatographed over silica gel (dichloromethanemethanol 9:1) to afford 6 g (20%) of the title compound, as an oil, which was characterized as the hydrochloride, m.p. 152°-155° C. (with decomposition) (after crystallization from ethanol-diethyl ether). NMR (DMSO-d$_6$, CDCl$_3$): delta$_H$=9.25 (b.s., 1H, CONH); 7.6-7.1 (c.a., 5H, PhH), 4.90 (t, J=6.1 Hz, 1H, NHCHNH); 4.17 (t, J=6.1 Hz, 1H, CHCH$_2$Ph); 3.84 (d, J=6.9 Hz, 2H, COOCH$_2$CH); 3.35 (c.a., 2H, CH$_2$Ph); 2.50-1.60 (c.a., 5H, CH$_2$CH$_2$COO, CH$_2$CH(CH$_3$)$_2$). MS (E.I., 70 eV, 1.5 mA) m/z=304 (M+), 213 M-C$_7$H$_7$)+, 84 (C$_3$H$_4$N$_2$O)+.

B) (3S)-3-Benzyl-2,5-dioxohexahydro-1H-pyrrolo[1,2-a]imidazole

A solution of isobutyl (4S)-4-benzyl-5-oxo-2-imidazolidinepropanoate (2.3 g, 7.33 mmol) in toluene (100 ml) was refluxed for 8 days. After evaporation of the solvent, the residue was chromatographed over silica gel (dichlorometane-methanol 9:1). The appropriate fractions were collected and evaporated; the residue was triturated with diethyl ether to afford 850 mg (50%) of the title compound, m.p. 141°-145° C. NMR (CDCl$_3$): delta$_H$=7.25 (s, 5H, PhH); 7.02 (b.s., 1H, NH); 4.52 (t, J=4.5 Hz, 1H, PhCH$_2$CH); 4.37 (t, J=5 Hz, 1H, NCHNH); 3.13 (d, J=4.5 Hz, 2H, PhCH$_2$); 2.80-1.6 (c.a., 4H, CH$_2$CH$_2$). MS (E.I., 70 eV, 1.5 mA) m/Z=230 (M+), 139 (M-C$_7$H$_7$)+, 91 (C$_7$H$_7$)+, 84 (C$_4$H$_6$NO)+.

EXAMPLE 13

(3S)-3-Hydroxymethyl-2,5-dioxohexahydro-1H-pyrrolo[1,2-a]imidazole

L-Serine hydrochloride (10 g, 0.071 mol) and isobutyl 4-oxo-butanoate (11.25 g, 0.071 mol) were reacted together according to the procedure of Example 2 to afford, after chromatography over silica gel (dichloromethane-methanol 8:2), 2.3 g (19%) of the title compound, m.p. 150°-162° C. NMR (DMSO-d$_6$): delta$_H$=8.57 b s., 1H, NH); 5.15 (t, J=5 Hz, 1H, N—CH—NH); 4.97 (ABCX System, 1H, CH$_2$OH); 3.88-3.81 (ABCX System, 1H, CHCH$_2$OH); 3.87-3.40 (ABCX System, 2H, CH$_2$OH); 2.85-1.52 (c.a., 4H, CH$_2$—CH$_2$). MS (E.I., 70 eV, 1.5 mA) m/z=140 (M-CH$_2$O)+, 84 (C$_3$H$_4$N$_2$O)+ and, as a by-product, 0.25 g of isobutyl (4S)-4-hydroxymethyl-5-oxo-2-imidazolidinepropanoate, m.p. 61°-75° C. NMR (DMSO-d$_6$): delta$_H$=8.1 (b.s., 1H, CONH); (c.a., 2H, NHCHNH, CH); 3.75 (d, J=6.1, 2H, COOCH$_2$CH); 3.55-2.90 (c.a., 4H, NH, CH—CH$_2$—OH); 2.50-2.30 (c.a., 2H, CH$_2$COO); 2.00-1.40 (c.a., 3H, CH(CH$_3$)$_2$, CH$_2$CH$_2$COO); 0.84 (d, J=6.1 Hz, 6H, CH(CH$_3$)$_2$). MS (E.I., 70 eV, 1.5 mA) m/z=213 (M-CH$_2$OH)+, 115 (C$_6$H$_{11}$O$_2$)+, 85 (C$_3$H$_5$N$_2$O)+.

EXAMPLE 14

A) 2-Carboxy-4-oxo-2-imidazolidinepropanoic acid

A solution of 2-oxoglutaric acid (10 g, 0.068 mol), glycinamide hydrochloride (8.3 g, 0.075 mol) and sodium hydroxide (8.2 g, 0.205 mol) in water (120 mol) was refluxed for 4 hours. After cooling the solution was adjusted to pH 2.5 and the resulting precipitate was collected and dried under vacuum at 60° C. to afford 5.9 g (43%) of the title compound, m.p. 202°–205° C. NMR (DMSO-d$_6$): delta$_H$=8.5 (s, 1H, CONH); 7.00–4.00 (b.s., 3H, NH, COOH); 3.22 and 3.18 (ABq, J=16 Hz, 2H, NHCH$_2$CO); 2.40–1.75 (c.a., 4H, CH$_2$CH$_2$COOH). MS (E.I., 70 eV, 1.5 mA) m/z=140 (M-H$_2$O-COOH)+, 84 (C$_3$H$_4$N$_2$O)+.

B) 2,5-Dioxohexahydro-1H-pyrrolo[1,2-a]imidazole-7a-carboxylic acid

A mixture of 2-carboxy-4-oxo-2-imidazolidine-propanoic acid (2 g, 9.89 mmol), hexamethyldisilazane (20 mol) and trimethylchlorosilane (10 ml) in dry acetonitrile (50 ml) was refluxed under nitrogen for 4 hours. After cooling, the precipitate was filtered off and the filtrate was evaporated under vacuum. The residue was dissolved in methanol (20 ml) containing some drops of concentrated hydrochloric acid and stirred for 10 minutes. The insoluble material was filtered off and the filtrate was evaporated to dryness. The residue was triturated with acetonitrile and crystallized with tetrahydrofuran (250 ml) to yield 0.9 g (50%) of the title compound, m.p. 207° C. (with decomposition). NMR (DMSO-d$_6$): delta$_H$: 9.20 (b.s., 1H, NH); 3.82 and 3.46 (ABq, J=16.8 Hz, 2H, NCH$_2$CO); 2.90–1.80 (c.a., 4H, CH$_2$—CH$_2$). MS (E.I., 70 eV, 1.5 mA) m/z=184 (M+), 139 (M-COOH)+, 83 (C$_3$H$_3$N$_2$O)+.

EXAMPLE 15

Ethyl 2,5-dioxohexahydro-1H-pyrrolo[1,2-a]imidazole-7a-carboxylate

A solution of 2,5-dioxohexahydropyrrolo-1H-[1,2-a]-imidazole-7a-carboxylic acid (0.8 g, 4.34 mmol) in dry tetrahydrofuran (100 ml), was cooled to 0° C., treated with oxalyl chloride (0.56 g, 4.34 mmol) and a drop of dimethylformamide and stirred for 2 hours at 0° C. The solution was stirred under vacuum at room temperature for 10 minutes. After cooling to 0° C., 4-dimethylaminopyridine (0.53 g, 4.34 mmol) and dry ethanol (2 ml) were added. The suspension was stirred at 0° C. for 30 minutes and at room temperature for 30 minutes. The precipitate was filtered off and the filtrate was evaporated under vacuum. The residue was chromatographed over silica gel (ethyl acetate-methanol 95:5) to afford 0.45 g (49%) of the title compound, m.p. 116° C. NMR (DMSO-d$_6$): delta$_H$=9.22 (b.s., 1H, NH); 4.16 (q, J=7.4 Hz, 2H, COOCH$_2$CH$_3$); 3.85 and 3.48 (ABq, J=14.8, 2H, NCH$_2$CO); 2.95–2.05 (c.a., 4H, CH$_2$CH$_2$); 1.2 (t, J=7.4 Hz, 3H, COOCH$_2$CH$_3$). MS (E.I., 70 eV, 1.5 mA) m/z=183 (M-C$_2$H$_5$)+, 139 (M-COOC$_2$H$_5$)+, 83 (C$_3$H$_3$N$_2$O)+.

EXAMPLE 16

2,5-Dioxohexahydro-1H-pyrrolo[1,2-a]imidazole-7a-carboxamide

An ice cold solution of ethyl 2,5-dioxo-1H-hexahydropyrrolo [1,2-a]imidazole-7a-carboxylate (2,55 g, 12 mmol) in dry methanol (20 ml) was treated with a saturated solution of ammonia in methanol (40 ml) and stirred for 1 hour at 0° C. The precipitate was collected, washed with acetone and dried to afford 1.7 g (77%) of the title compound m.p. 295° C. (with decomposition). NMR (DMSO-d$_6$): delta$_H$=9.05 (b.s., 1H, NH); 7.50 (b.s., 2H, CONH$_2$); 3.80 and 3.50 (ABq, J=14.8 Hz, 2H, NCH$_2$CO); 2.85–1.95 (c.a., 4H, CH$_2$CH$_2$). MS (E.I., 70 eV, 1.5 mA) m/z=139 (M-CONH$_2$)+, 83 (C$_3$H$_3$N$_2$O)+.

EXAMPLE 17

2,5-Dioxo-1H-octahydroimidazo[1,2-a]pyridine

Glycinamide hydrochloride (4.24 g, 38.4 mmol) and methyl 5-oxopentanoate (5 ml, 38.4 mmol) were reacted together according to the procedure of example 2, to give 1.8 g (30%) of the title compound, m.p. 170°–174° C. NMR NMR (DMSO-d$_6$):delta$_H$=8.65. (b.s., 1H, CONH); 5.10–4.85 (c.a., 1H, NCHNH); 3.90 and 3.55 (ABq, J=14.8 Hz, 2H, N—CH$_2$—CO); 2.40–1.10 (c.a., 6H, CH$_2$CH$_2$CH$_2$). MS (E.I., 70 eV, 1.5 mA) m/z=153 (M-H)+, 111 (M-CONH)+, 84 (C$_3$H$_4$N$_2$O)+.

EXAMPLE 18

A) Methyl 4-oxo-2-imidazolidinepentanoate

Glycinamide hydrochloride (6.73 g, 0.061 mol) and methyl 6-oxohexanoate (8.8 ml, 0.061 mol) were reacted together according to the procedure of example 2, to give 0.93 (7.6%) of the title compound, m.p. 58°–60° C. (with decomposition). NMR (DMSO-d$_6$): delta$_H$=8.10 (b.s., 1H, CONH); 4.50–4.15 (c.a., 1H, NHCHNH); 3.55 (s, 3H, COOCH$_3$); 3.20 (b.s., 1H, CH$_2$NHCH); 3.05 (s, 2H, NHCH$_2$CO); 2.45–2.10 (c.a., 2H, CH$_2$COO); 1.80–1.10 (c.a., 6H, CH$_2$CH$_2$CH$_2$CH$_2$COO). MS (E.I., 70 eV, 1.5 mA) m/z=200 (M+), 169 (M-OCH$_3$)+, 85 (C$_3$H$_5$N$_2$O)+.

B) 2,5-Dioxo-1H-octahydroimidazo[1,2-a]azepine

A solution of methyl 4-oxo-2-imidazolidinepentanoate (1 g, 5 mmol) in toluene (300 ml) was refluxed for 80 hours. After cooling the solution was evaporated and the residue was chromatographed over silica gel (dichloromethane-methanol 9:1) to afford 0.2 g (23%) of the title compound, m.p. 175°–176° C. NMR (DMSO-d$_6$) delta$_H$=8.60 (b.s., 1H, CONH); 5.35–5.10 (c.a., 1H, NCHNH); 3.70 (s, 2H, NCH$_2$CO); 2.60–2.10 (c.a., 2H, CH$_2$CH$_2$CON); 2.10–1.10 (c.a., 6H, CH$_2$CH$_2$CH$_2$). MS (E.I., 70 eV, 1.5 mA) m/z=168 (M+), 85 (C$_3$H$_5$N$_2$O)+.

EXAMPLE 19

A) Isobutyl 3-benzyl-5-oxo-2-imidazolidinepropanoate hydrochloride

A solution of N-benzylglycinamide (3.7 g, 0.022 mol) and isobutyl 4-oxobutanoate (4 g, 0.023 mol) in dioxane (40 mol) and water (10 ml) was heated at 100° C. for 10 hours. After cooling, the solvent was removed under vacuum and the residue was treated with 10% hydrochloric acid (6 ml) to give a precipitate which was collected and triturated with acetone to afford 3.6 g (47%) of the title compound, m.p. 177° C. (with decomposition). NMR (DMSO-d$_6$): delta$_H$=9.2 (b.s., 1H, NH); 7.80–7.30 (c.a, 5H, PhH); 4.90 (t, J=5 Hz, 1H, N—CH—NH); 4.50 and 4.30 (ABq, J=13.6 Hz, 2H, CH$_2$Ph); 3.80 (d, J=6.1 Hz, 2H, COOCH$_2$CH); 3.68 (s, 2H, CONH$_2$N); 2.65–2.35 (c.a., 2H, CH$_2$CH$_2$COO); 2.20–1.50 (c.a., 3H, CH(CH$_3$)$_2$ and CH$_2$CH$_2$COO); 0.88 (d, J=6.1 Hz, 6H, CH(CH$_3$)$_2$). MS (E.I., 70 eV, 1.5 mA) m/z=304 (M+), 175 (M-C$_7$H$_{13}$O$_2$)+, 91 (C$_7$H$_7$)+.

B) Isobutyl 5-oxo-2-imidazolidinepropanoate hydrochloride

To a mixture of 10% palladium on charcoal (1 g) and 99% formic acid (1 ml) in methanol (25 ml), under nitrogen, was added a solution of isobutyl 3-benzyl-5-oxo-2- imidazolidinepropanoate hydrochloride (1 g, 2.93 mmol) and 99% formic acid (1.25 ml) in methanol (25 ml). The mixture was stirred under nitrogen for 6 hours. After addition of water (15 ml) and removal of the catalyst, the solvent was evaporated and the residue was triturated with ethanol to give 0.3 g (41%) of the title compound, m.p. 136°–140° C. The same compound was obtained also by the following procedure: into a mixture of isobutyl 3-benzyl-5-oxo-2-imidazolidine-propanoate hydrochloride (2.2 g, 6.4 mmol), and 10% palladium on charcoal (1.1 g) in water-methanol 2:1 (150 ml) hydrogen was bubbled at room temperature and at atmospheric pressure for 2 hours. Removal of the catalyst and evaporation of the solvent under reduced pressure gave a residue which was triturated with ethanol to afford 1.4 g (90%) of the title compound, m.p.136°–140° C. NMR (DMSO-d$_6$): delta$_H$=11.1–9.50 (b.s., 2H, NH$_2$+); 9.20 (b.s., 1H, CONH); 4.95 (t, J=6.2 Hz, 1H, NHC$\underline{H}$NH); 3.84 (d, J=6.7 Hz, 2H, COOC$\underline{H}_2$); 3.65 (s, 2$\overline{H}$, NCH$_2$CO); 2.70–2.30 (c.a., 2H, CH$_2$C$\underline{H}_2$COO); 2.25–1.60 (c.a., 3H, CH$_2$CH$_2$COO, C$\underline{H}$(CH$_3$)$_2$); 0.87 (d, J=6.7 Hz, 6H, CH(C$\underline{H}_3$)$_2$. MS (E.I., 70 eV, 1.5 mA) m/z=214 (M+), 141 (M-OC$_4$H$_9$)+, 85 (C$_3$H$_5$N$_2$O)+.

C) 2,5-Dioxohexahydro-1H-pyrrolo[1,2-a]imidazole

A solution of isobutyl 5-oxo-2-imidazolidinepropanoate hydrochloride (1.4 g, 5.76 mmol) in water (100 ml) was treated with sodium hydrogen carbonate (0.54 g, 6.4 mmol) and heated at 100° C. for 20 hours. The solution was evaporated and the residue was chromatographed over silica gel (ethyl acetate-acetone-methanol 6:3:1) to afford 300 mg (37%) of the title compound, m.p. 155°–157° C.

EXAMPLE 20

A) Ethyl 1-benzyl-4-oxo-2-imidazolidinepropanoate

A suspension of N-benzylglycinamide (35.5 g, 0.22 mol) and ethyl 4-oxobutanoate (31 g, 0.24 mol) in toluene (370 ml) was refluxed for 6 hours in a Dean-Stark apparatus. After cooling, the mixture was extracted twice with 10% sulphuric acid (200+100 ml); the aqueous extracts were neutralized with sodium hydrogen carbonate and extracted twice with toluene (250 ml each time). The organic solution was washed with water (100 ml), dried (MgSO$_4$) and evaporated under vacuum to afford an oil which was triturated with a mixture of diethyl ether-light petroleum (1:2) to give 45 g (75%), of the title compound as a yellow solid, m.p. 60°–62° C. NMR (CDCl$_3$): delta$_H$=7.5 (bs, 1H, N$\underline{H}$); 7.30 (bs, 5H, Ph$\underline{H}$); 4.5–4.25 (ABX, 1H, C$\underline{H}$-M); 4.13 (q, J=6.9 Hz, 2H, OC$\underline{H}_2$); 4.00 and 3.53 (ABq, J=12.4 Hz, 2H, PhC$\underline{H}_2$); 3.37 and 3.02 (ABX, J=14.9 Hz, 2H, NC$\underline{H}_2$CO); 2.65–2.30 (c.a., 2H, C$\underline{H}_2$CH$_2$CO); 2.20–1.15 (c.a., 2H, CH$_2$C$\underline{H}_2$CO); 1.24 (t, J=6.9 Hz, 3H, C$\underline{H}_3$). MS (E.I., 70 eV, 1.5 mA) m/z=276 (M+), 231 (M-OEt)+, 185 (M-PhCH$_2$)+, 175 (M-C$_5$H$_9$O$_2$)+, 91 (PhCH$_2$)+.

B) 2,5-Dioxohexahydro-1H-pyrrolo[1,2-a]imidazole

To a suspension of 10% palladium on charcoal (11.6 g) in water (60 ml), a solution of ethyl 3-benzyl-5-oxo-2-imidazolidinepropanoate (58 g, 0.21 mol) and ammonium formate (52.9 g, 0.84 mol) in methanol (580 ml) were added. The mixture was refluxed under nitrogen for 1 hour. After cooling to 40° C., 32% ammonia (145 ml) was added and the temperature was maintained between 40° and 50° C. for 1.5 hours. After cooling to room temperature, the catalyst was removed by filtration and the solution was evaporated to dryness. The residue was diluted with water (700 ml) and stirred in the presence of ion exchange resins Amberlite IR 120 H (200 ml) and Amberlite IRA 68 (200 ml) for 1.5 hours. The resins were filtered off and washed with water (600 ml). The clear solution was evaporated under vacuum at 60° C. to afford an oil which was dried by azeotropic distillation with ethanol. The resulting residue was triturated with acetone (75 ml) to afford 19.7 g (67%) of the title compound as a white solid, m.p. 154°–157° C.

What is claimed is:

1. A compound of structure (1)

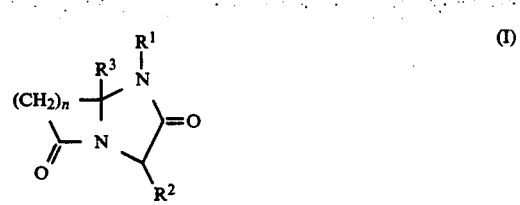

wherein

R$^1$ is hydrogen, C$_{1-4}$ alkyl, CHR$^6$CONHR$^7$ $^1$ or CHR$^6$COOR$^7$ in which R$^6$ and R$^7$ are each hydrogen or C$_{1-4}$ alkyl;

R$^2$ is hydrogen, C$_{1-5}$ alkyl, C$_6$H$_5$CH$_2$, CH$_2$OH, CH$_2$CH$_2$CONH$_2$ or CH$_2$COOH;

R$^3$ is hydrogen, C$_{1-4}$ alkyl, CONH$_2$ or CO$_2$R$^8$ in which R$^8$ is hydrogen, or C$_{1-4}$ alkyl, and n is 4;

or a pharmaceutically acceptable salt thereof.

2. A compound of structure (1) as claimed in claim 1 in which R$^1$ to R$^3$ are each hydrogen.

3. The compound according to claim 1 wherein R$^2$ is hydrogen, or C$_{1-5}$ alkyl.

4. The compound according to claim 3 wherein R$^2$ is —CH$_3$, or —CH(CH$_3$)$_2$.

5. A compound of structure (1) as claimed in claim 1 which is:

2,5-dioxo-1H-octahydroimidazo[1,2-a]azepine.

6. A pharmaceutical composition comprising a compound of structure (1) or a pharmaceutically acceptable salt thereof as claimed in claim 1 and a pharmaceutically acceptable carrier.

7. A pharmaceutical composition according to claim 6 wherein the compound of structure (1) is 2,5-dioxo-1H-octahydroimidazo[1,2-a]azepine.

8. A method of restoring learning and treating memory difficulties which comprises administering to a subject in need thereof a non-toxic effective amount of a compound of structure (1) as described in claim 1.

* * * * *